US008923945B2

(12) United States Patent
McKenna

(10) Patent No.: US 8,923,945 B2
(45) Date of Patent: Dec. 30, 2014

(54) DETERMINATION OF A PHYSIOLOGICAL PARAMETER

(75) Inventor: Edward M. McKenna, Boulder, CO (US)

(73) Assignee: Covidien LP, Mansfield, MA (US)

( * ) Notice: Subject to any disclaimer, the term of this patent is extended or adjusted under 35 U.S.C. 154(b) by 835 days.

(21) Appl. No.: 12/880,303

(22) Filed: Sep. 13, 2010

(65) Prior Publication Data

US 2011/0071366 A1 Mar. 24, 2011

Related U.S. Application Data

(60) Provisional application No. 61/245,573, filed on Sep. 24, 2009.

(51) Int. Cl.
*A61B 5/1455* (2006.01)
*G06T 11/20* (2006.01)
*A61B 5/00* (2006.01)

(52) U.S. Cl.
CPC ........... *G06T 11/206* (2013.01); *A61B 5/14551* (2013.01); *A61B 5/726* (2013.01)
USPC ............ 600/336; 600/310; 600/322; 600/323

(58) Field of Classification Search
USPC ......... 600/310, 322, 323, 324, 331, 473, 476, 600/336; 356/41
See application file for complete search history.

(56) References Cited

U.S. PATENT DOCUMENTS

| 3,638,640 | A | 2/1972 | Shaw |
| 4,289,141 | A | 9/1981 | Cormier |
| 4,700,708 | A | 10/1987 | New, Jr. et al. |
| 4,936,679 | A | 6/1990 | Mersch |
| 4,942,877 | A | 7/1990 | Sakai et al. |

(Continued)

FOREIGN PATENT DOCUMENTS

| EP | 1740095 | 1/2007 |
| JP | 25095581 A2 | 4/2005 |

(Continued)

OTHER PUBLICATIONS

Barnum P.T. et al.; "Novel Pulse Oximetry Technology Capable of Reliable Bradycardia Monitoring in the Neonate" *Respiratory Care* vol. 42 No. 1 p. 1072 (Nov. 1997).

(Continued)

*Primary Examiner* — Eric Winakur
*Assistant Examiner* — Chu Chuan (JJ) Liu
(74) *Attorney, Agent, or Firm* — Fletcher Yoder PC

(57) ABSTRACT

Methods and systems are provided for transmitting and receiving photon density waves to and from tissue, and processing the received waves using wavelet transforms to identify non-physiological signal components and/or identify physiological conditions. A pulse oximeter may receive the photon density waves from the tissue to generate a signal having phase and amplitude information. A phase signal may be proportional to a scattering by total particles in the tissue, and an amplitude signal may correlate to an absorption by certain particles, providing information on a ratio of different particles in the tissue. Processing the phase and amplitude signals with wavelet transforms may enable an analysis of signals with respect to time, frequency, and magnitude, and may produce various physiological data. For example, non-physiological noise components may be identified, and certain physiological conditions may be identified by processing scalograms of the original signals with patterns corresponding to certain physiological conditions.

11 Claims, 12 Drawing Sheets

(56) References Cited

U.S. PATENT DOCUMENTS

| | | | |
|---|---|---|---|
| 4,971,062 A | 11/1990 | Hasebe et al. | |
| 4,974,591 A | 12/1990 | Awazu et al. | |
| 5,028,787 A | 7/1991 | Rosenthal et al. | |
| 5,058,588 A | 10/1991 | Kaestle | |
| 5,065,749 A | 11/1991 | Hasebe et al. | |
| 5,084,327 A | 1/1992 | Stengel | |
| 5,275,159 A | 1/1994 | Griebel | |
| 5,439,483 A | 8/1995 | Duong-Van | |
| 5,483,646 A | 1/1996 | Uchikoga | |
| 5,497,769 A * | 3/1996 | Gratton et al. | 600/323 |
| 5,590,650 A | 1/1997 | Genova | |
| 5,730,124 A | 3/1998 | Yamauchi | |
| 5,778,881 A | 7/1998 | Sun et al. | |
| 5,779,631 A | 7/1998 | Chance | |
| 5,795,304 A | 8/1998 | Sun et al. | |
| 5,797,840 A | 8/1998 | Akselrod et al. | |
| 5,827,195 A | 10/1998 | Lander | |
| 5,830,139 A | 11/1998 | Abreu | |
| 5,831,598 A | 11/1998 | Kauffert et al. | |
| 5,871,442 A | 2/1999 | Madarasz et al. | |
| 5,873,821 A | 2/1999 | Chance et al. | |
| 5,957,866 A | 9/1999 | Shapiro et al. | |
| 5,967,995 A | 10/1999 | Shusterman et al. | |
| 6,002,952 A | 12/1999 | Diab et al. | |
| 6,067,462 A | 5/2000 | Diab et al. | |
| 6,081,742 A | 6/2000 | Amano et al. | |
| 6,095,984 A | 8/2000 | Amano et al. | |
| 6,117,075 A | 9/2000 | Barnea | |
| 6,120,460 A | 9/2000 | Abreu | |
| 6,129,675 A | 10/2000 | Jay | |
| 6,134,460 A | 10/2000 | Chance | |
| 6,135,966 A | 10/2000 | Ko | |
| 6,208,951 B1 | 3/2001 | Kumar et al. | |
| 6,285,895 B1 | 9/2001 | Ristolainen et al. | |
| 6,293,915 B1 | 9/2001 | Amano et al. | |
| 6,312,393 B1 | 11/2001 | Abreu | |
| 6,325,761 B1 | 12/2001 | Jay | |
| 6,353,750 B1 | 3/2002 | Kimura et al. | |
| 6,361,501 B1 | 3/2002 | Amano et al. | |
| 6,415,236 B2 | 7/2002 | Kobayashi et al. | |
| 6,419,671 B1 | 7/2002 | Lemberg | |
| 6,461,305 B1 | 10/2002 | Schnall | |
| 6,487,439 B1 | 11/2002 | Skladnev et al. | |
| 6,519,486 B1 | 2/2003 | Edgar, Jr. et al. | |
| 6,544,193 B2 | 4/2003 | Abreu | |
| 6,549,795 B1 | 4/2003 | Chance | |
| 6,561,986 B2 | 5/2003 | Baura et al. | |
| 6,571,193 B1 | 5/2003 | Unuma et al. | |
| 6,591,122 B2 | 7/2003 | Schmitt | |
| 6,606,509 B2 | 8/2003 | Schmitt | |
| 6,608,934 B2 | 8/2003 | Scheirer et al. | |
| 6,618,042 B1 | 9/2003 | Powell | |
| 6,622,095 B2 | 9/2003 | Kobayashi et al. | |
| 6,654,623 B1 | 11/2003 | Kastle | |
| 6,662,030 B2 | 12/2003 | Khalil et al. | |
| 6,675,029 B2 | 1/2004 | Monfre et al. | |
| 6,687,519 B2 | 2/2004 | Steuer et al. | |
| 6,690,958 B1 | 2/2004 | Walker et al. | |
| 6,699,194 B1 | 3/2004 | Diab et al. | |
| 6,714,245 B1 | 3/2004 | Ono | |
| 6,731,274 B2 | 5/2004 | Powell | |
| 6,785,568 B2 | 8/2004 | Chance | |
| 6,793,654 B2 | 9/2004 | Lemberg | |
| 6,810,277 B2 | 10/2004 | Edgar, Jr. et al. | |
| 6,850,053 B2 | 2/2005 | Daalmans et al. | |
| 6,898,451 B2 | 5/2005 | Wuori | |
| 6,909,808 B2 * | 6/2005 | Stanek | 382/232 |
| 6,931,269 B2 | 8/2005 | Terry | |
| 6,949,081 B1 | 9/2005 | Chance | |
| 6,961,742 B2 | 11/2005 | Neretti et al. | |
| 7,020,507 B2 | 3/2006 | Scharf et al. | |
| 7,035,679 B2 | 4/2006 | Addison et al. | |
| 7,035,697 B1 | 4/2006 | Brown | |
| 7,041,063 B2 | 5/2006 | Abreu | |
| 7,043,289 B2 | 5/2006 | Fine et al. | |
| 7,043,293 B1 | 5/2006 | Baura | |
| 7,054,453 B2 | 5/2006 | Causevic et al. | |
| 7,054,454 B2 | 5/2006 | Causevic et al. | |
| 7,065,392 B2 | 6/2006 | Kato | |
| 7,072,702 B2 | 7/2006 | Edgar, Jr. et al. | |
| 7,079,888 B2 | 7/2006 | Oung et al. | |
| 7,095,491 B2 | 8/2006 | Forstner et al. | |
| 7,171,269 B1 | 1/2007 | Addison et al. | |
| 7,203,267 B2 | 4/2007 | De Man et al. | |
| 7,215,984 B2 | 5/2007 | Diab et al. | |
| 7,215,986 B2 | 5/2007 | Diab et al. | |
| 7,225,013 B2 | 5/2007 | Geva et al. | |
| 7,236,811 B2 | 6/2007 | Schmitt | |
| 7,239,902 B2 | 7/2007 | Schmitt et al. | |
| 7,254,433 B2 | 8/2007 | Diab et al. | |
| 7,254,500 B2 | 8/2007 | Makeig et al. | |
| 7,272,426 B2 | 9/2007 | Schmid | |
| 7,289,835 B2 | 10/2007 | Mansfield et al. | |
| 7,376,453 B1 | 5/2008 | Diab et al. | |
| 7,383,070 B2 | 6/2008 | Diab et al. | |
| 7,469,158 B2 | 12/2008 | Cutler et al. | |
| 7,519,488 B2 | 4/2009 | Fu et al. | |
| 7,523,011 B2 | 4/2009 | Akiyama et al. | |
| 7,551,950 B2 | 6/2009 | Cheng | |
| 7,621,877 B2 | 11/2009 | Schnall | |
| 2002/0042558 A1 | 4/2002 | Mendelson | |
| 2002/0156354 A1 | 10/2002 | Larson | |
| 2002/0183601 A1 * | 12/2002 | Tearney et al. | 600/310 |
| 2002/0198443 A1 | 12/2002 | Ting | |
| 2003/0023140 A1 | 1/2003 | Chance | |
| 2003/0225337 A1 | 12/2003 | Scharf et al. | |
| 2004/0171920 A1 | 9/2004 | Mannheimer et al. | |
| 2004/0204637 A1 | 10/2004 | Diab et al. | |
| 2005/0033129 A1 | 2/2005 | Edgar et al. | |
| 2005/0043763 A1 | 2/2005 | Marcovecchio et al. | |
| 2005/0049470 A1 | 3/2005 | Terry et al. | |
| 2005/0070774 A1 | 3/2005 | Addison et al. | |
| 2005/0113651 A1 | 5/2005 | Wood et al. | |
| 2005/0113656 A1 | 5/2005 | Chance | |
| 2005/0192488 A1 | 9/2005 | Bryenton et al. | |
| 2005/0209517 A1 | 9/2005 | Diab et al. | |
| 2005/0228248 A1 | 10/2005 | Dietiker | |
| 2006/0009809 A1 | 1/2006 | Marcovecchio et al. | |
| 2006/0020181 A1 | 1/2006 | Schmitt | |
| 2006/0122475 A1 | 6/2006 | Balberg et al. | |
| 2006/0149144 A1 | 7/2006 | Lynn et al. | |
| 2006/0155206 A1 | 7/2006 | Lynn et al. | |
| 2006/0161071 A1 | 7/2006 | Lynn et al. | |
| 2006/0200016 A1 | 9/2006 | Diab et al. | |
| 2006/0209631 A1 | 9/2006 | Melese et al. | |
| 2006/0211930 A1 | 9/2006 | Scharf et al. | |
| 2006/0217609 A1 | 9/2006 | Diab et al. | |
| 2006/0229519 A1 | 10/2006 | Fujiwara et al. | |
| 2006/0235324 A1 | 10/2006 | Lynn et al. | |
| 2006/0247501 A1 | 11/2006 | Ali | |
| 2006/0247506 A1 | 11/2006 | Balberg et al. | |
| 2006/0258921 A1 | 11/2006 | Addison et al. | |
| 2006/0258927 A1 | 11/2006 | Edgar, Jr. et al. | |
| 2006/0265022 A1 | 11/2006 | John et al. | |
| 2007/0004977 A1 | 1/2007 | Norris et al. | |
| 2007/0021673 A1 | 1/2007 | Arbel et al. | |
| 2007/0073120 A1 | 3/2007 | Li et al. | |
| 2007/0073124 A1 | 3/2007 | Li et al. | |
| 2007/0129647 A1 | 6/2007 | Lynn et al. | |
| 2007/0167694 A1 | 7/2007 | Causevic et al. | |
| 2007/0191688 A1 | 8/2007 | Lynn | |
| 2007/0191697 A1 | 8/2007 | Lynn et al. | |
| 2007/0219059 A1 | 9/2007 | Schwartz et al. | |
| 2007/0225581 A1 | 9/2007 | Diab et al. | |
| 2007/0249918 A1 | 10/2007 | Diab et al. | |
| 2007/0282212 A1 | 12/2007 | Sierra et al. | |
| 2007/0291832 A1 | 12/2007 | Diab et al. | |
| 2008/0004514 A1 | 1/2008 | Diab et al. | |
| 2008/0033266 A1 | 2/2008 | Diab et al. | |
| 2008/0036752 A1 | 2/2008 | Diab et al. | |
| 2008/0045823 A1 | 2/2008 | Diab et al. | |
| 2008/0045832 A1 | 2/2008 | Mcgrath et al. | |
| 2008/0066753 A1 | 3/2008 | Martin et al. | |

(56) References Cited

U.S. PATENT DOCUMENTS

| | | | |
|---|---|---|---|
| 2008/0082018 | A1 | 4/2008 | Sackner et al. |
| 2008/0214903 | A1 | 9/2008 | Orbach et al. |
| 2011/0071376 | A1 | 3/2011 | Mckenna |

FOREIGN PATENT DOCUMENTS

| | | | |
|---|---|---|---|
| WO | WO9309711 | | 5/1993 |
| WO | WO9608992 | A2 | 3/1996 |
| WO | WO9842249 | | 10/1998 |
| WO | WO9842251 | | 10/1998 |
| WO | WO0077675 | A1 | 12/2000 |
| WO | WO0125802 | A2 | 4/2001 |
| WO | WO0162152 | A1 | 8/2001 |
| WO | WO0176461 | | 10/2001 |
| WO | WO0182099 | A1 | 11/2001 |
| WO | WO03000125 | | 1/2003 |
| WO | WO03055395 | | 7/2003 |
| WO | WO2004075746 | | 9/2004 |
| WO | WO2004105601 | | 12/2004 |
| WO | WO2005096931 | | 10/2005 |
| WO | WO2006085120 | | 8/2006 |
| WO | WO2007131064 | A2 | 11/2007 |
| WO | WO2007131066 | A2 | 11/2007 |

OTHER PUBLICATIONS

Masin Donald I. et al.; "Fetal Transmission Pulse Oximetry" *Proceedings 19th International Conference IEEE/EMBS* Oct. 30-Nov. 2, 1997; pp. 2326-2329.

Leahy Martin J. et al.; "Sensor Validation in Biomedical Applications" *IFAC Modelling and Control in Biomedical Systems* Warwick UK; pp. 221-226 (1997).

Barreto Armando B. et al.; "Adaptive LMS Delay Measurement in dual Blood Volume Pulse Signals for Non-Invasive Monitoring" *IEEE* pp. 117-120 (1997).

East Christine E. et al.; "Fetal Oxygen Saturation and Uterine Contractions During Labor" American Journal of Perinatology vol. 15 No. 6 pp. 345-349 (Jun. 1998).

Edrich Thomas et al.; "Can the Blood Content of the Tissues be Determined Optically During Pulse Oximetry Without Knowledge of the Oxygen Saturation?—An In-Vitro Investigation" Proceedings of the 20th Annual International conference of the IEEE Engie.

Such Hans Olaf; "Optoelectronic Non-invasive Vascular Diagnostics Using multiple Wavelength and Imaging Approach" Dissertation (1998).

Lutter N. et al.; "Comparison of Different Evaluation Methods for a Multi-wavelength Pulse Oximeter" Biomedizinische Technik vol. 43 (1998).

Rhee Sokwoo et al.; "Design of a Artifact-Free Wearable Plethysmographic Sensor" Proceedings of the First joint BMES/EMBS Conference Oct. 13-16, 1999 Altanta Georgia p. 786.

Rheineck-Leyssius Aart t. et al.; "Advanced Pulse Oximeter Signal Processing Technology Compared to Simple Averaging: I. Effect on Frequency of Alarms in the Operating Room" Journal of clinical Anestesia vol. 11 pp. 192-195 (1999).

Kaestle S.; "Determining Artefact Sensitivity of New Pulse Oximeters in Laboratory Using Signals Obtained from Patient" Biomedizinische Technik vol. 45 (2000).

Tremper K.K.; "A Second Generation Technique for Evaluating Accuracy and Reliability of Second Generation Pulse Oximeters" Journal of Clinical Monitoring and Computing vol. 16 pp. 473-474 (2000).

Maletras Francois-Xavier et al.; "Construction and calibration of a new design of Fiber Optic Respiratory Plethysmograph (FORP)" *Optomechanical Design and Engineering Proceedings of SPIE* vol. 4444 pp. 285-293 (2001).

Cysewska-Sobusaik Anna; "Metrological Problems With noninvasive Transillumination of Living Tissues" *Proceedings of SPIE* vol. 4515 pp. 15-24 (2001).

Yao Jianchu et al.; "Design of a Plug-and-Play Pulse Oximeter" Proceedings of the Second Joint EMBS/BMES Conference Houston Texas Oct. 23-26, 2002; pp. 1752-1753.

Jopling Michae W. et al.; "Issues in the Laboratory Evaluation of Pulse Oximeter Performance" Anesth Analg vol. 94 pp. S62-S68 (2002).

Yamaya Yoshiki et al.; "Validity of pulse oximetry during maximal exercise in normoxia hypoxia and hyperoxia" J. Appl. Physiol. vol. 92 pp. 162-168 (2002).

Yoon Gilwon et al.; Multiple diagnosis based on Photoplethysmography: hematocrit SpO2 pulse and respiration Optics in Health Care and Biomedical optics: Diagnostics and Treatment; Proceedings of the SPIE vol. 4916; pp. 185-188 (2002).

Cyrill D. et al.; "Adaptive Comb Filter for Quasi-Periodic Physiologic Signals" Proceedings of the 25th Annual International Conference of the IEEE EMBS Cancun Mexico Sep. 17-21, 2003; pp. 2439-2442.

Stetson Paul F.; "Determining Heart Rate from Noisey Pulse Oximeter Signals Using Fuzzy Logic" The IEEE International Conference on Fuzzy Systems St. Louis Missouri May 25-28, 2003; pp. 1053-1058.

Aoyagi Takuo; "Pulse oximetry: its invention theory and future" Journal of Anesthesia vol. 17 pp. 259-266 (2003).

Lee C.M. et al.; "Reduction of motion artifacts from photoplethysmographic recordings using wavelet denoising approach" IEEE EMBS Asian-Pacific Conference on Biomedical Engineering Oct. 20-22, 2003; pp. 194-195.

A. Johansson; "Neural network for photoplethysmographic respiratory rate monitoring" Medical & Biological Engineering & Computing vol. 41 pp. 242-248 (2003).

Addison Paul S. et al.; "A novel time-frequency-based 3D Lissajous figure method and its application to the determination of oxygen saturation from the photoplethysmogram" Institute of Physic Publishing Meas. Sci. Technol. vol. 15 pp. L15-L18 (2004).

Matsuzawa Y. et al.; "Pulse Oximeter" *Home Care Medicine* pp. 42-45 (Jul. 2004); (Article in Japanese—contains English summary of article).

Pickett, John, et al.; "Pulse Oximetry and PPG Measurements in Plastic Surgery," Proceedings—19th International Conference—IEEE/EMBS, Chicago, Illinois, Oct. 30-Nov. 2, 1997, pp. 2330-2332.

Todd, Bryan, et al.; "The Identification of Peaks in Physiological Signals," Computers and Biomedical Research, vol. 32, pp. 322-335 (1999).

Seelbach-Gobel, Birgit, et al.; "The prediction of fetal acidosis by means of intrapartum fetal pulse oximetry," Am J. Obstet. Gynecol., vol. 180, No. 1, Part 1, pp. 73-81 (1999).

Goldman, Julian M.; "Masimo Signal Extraction Pulse Oximetry," Journal of Clinical Monitoring and Computing, vol. 16, pp. 475-483 (2000).

Coetzee, Frans M.; "Noise-Resistant Pulse Oximetry Using a Synthetic Reference Signal," IEEE Transactions on Biomedical Engineering, vol. 47, No. 8, Aug. 2000, pp. 1018-1026.

Nilsson, Lena, et al.; "Monitoring of Respiratory Rate in Postoperative Care Using a New Photoplethysmographic Technique," Journal of Clinical Monitoring and Computing, vol. 16, pp. 309-315 (2000).

Belal, Suliman Yousef, et al.; "A fuzzy system for detecting distorted plethysmogram pulses in neonates and paediatric patients," Physiol. Meas., vol. 22, pp. 397-412 (2001).

Earthrowl-Gould, T., et al.; "Chest and abdominal surface motion measurement for continuous monitoring of respiratory function," Proc. Instn Mech Engrs, V215, Part H; pp. 515-520 (2001).

Chan, K.W., et al.; "17.3: Adaptive Reduction of Motion Artifact from Photoplethysmographic Recordings using a Variable Step-Size LMS Filter," IEEE, pp. 1343-1346 (2002).

Relente, A.R., et al.; "Characterization and Adaptive Filtering of Motion Artifacts in Pulse Oximetry using Accelerometers," Proceedings of the Second joint EMBS/BMES Conference, Houston, Texas, Oct. 23-26, 2002; pp. 1769-1770.

Johnston, W.S., et al.; "Extracting Breathing Rate Infromation from a Wearable Reflectance Pulse Oximeter Sensor," Proceedings of the 26th Annual International conference of the IEEE EMBS, San Francisco, California; Sep. 1-5, 2004; pp. 5388-5391.

(56) References Cited

OTHER PUBLICATIONS

Spigulis, Janis, et al.; "Optical multi-channel sensing of skin blood pulsations," Optical Sensing, Proceedings of SPIE, vol. 5459, pp. 46-53 (2004).

Hamilton, Patrick S., et al.; "Effect of Adaptive Motion-Artifact Reduction on QRS Detection," Biomedical Instrumentation & Technology, pp. 197-202; 2000.

Kim J.M., et al.; "Signal Processing Using Fourier & Wavelet Transform," pp. II-310-II-311 2001.

Odagiri, Y.; "Pulse Wave Measuring Device," Micromechatronics, vol. 42, No. 3, pp. 6-11; 1998; (Article in Japanese—contains English summary of article).

Neumann, R., et al.; "Fourier Artifact suppression Technology Provides Reliable SpO2" Abstracts, A11, p. S105. 2002.

PCT International Search Report, Mar. 22, 2011; PCT/US2010/045572, filed Aug. 16, 2010.

Addison, P.S., et al.; "Oxygen saturation determined using a novel wavelet ratio surface," Medical Engineering & Physics, Butterworth-Heinemann, GB. vol. 27, No. 3, Apr. 1, 2005, pp. 245-248.

Leonard, Paul A., et al.; "A fully automated algorithm for the determination of respiratory rate from the photoplethysmogram," Journal of Clinical Monitoring and Computing, Kluwer Academic Publishers, vol. 20, No. 1, Feb. 1, 2006, pp. 33-36.

Leonard, P., et al.; "Wavelet analysis of pulse oximeter waveform permits identification of unwell children," Emergency Medicine Journal, vol. 21, No. 1, Jan. 2004.

Salamalekis, Emmanuel, et al.; "Fetal pulse oximetry and wavelet analysis of the fetal heart rate in the evaluation of abnormal cardiotocography tracings," The Journal of Obstetrics and Gynecology Research, Apr. 2008, vol. 32, No. 1, pp. 135-139.

\* cited by examiner

DETERMINATION OF A PHYSIOLOGICAL PARAMETER

RELATED APPLICATIONS

This application claims the benefit of U.S. Provisional Application No. 61/245,573, filed Sep. 24, 2009, which application is hereby incorporated by reference.

BACKGROUND

The present disclosure relates generally to medical devices and, more particularly, to methods of analyzing physiological parameters using photon density waves.

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

In the field of medicine, doctors often desire to monitor certain physiological characteristics of their patients. Accordingly, a wide variety of devices have been developed for monitoring many such physiological characteristics. Such devices provide doctors and other healthcare personnel with the information they need to provide the best possible healthcare for their patients. As a result, such monitoring devices have become an indispensable part of modern medicine.

One technique for monitoring certain physiological characteristics of a patient is commonly referred to as pulse oximetry, and the devices built based upon pulse oximetry techniques are commonly referred to as pulse oximeters. Pulse oximetry may be used to measure various blood flow characteristics, such as the blood-oxygen saturation of hemoglobin in arterial blood, the volume of individual blood pulsations supplying the tissue, and/or the rate of blood pulsations corresponding to each heartbeat of a patient. In fact, the "pulse" in pulse oximetry refers to the time varying amount of arterial blood in the tissue during each cardiac cycle.

Pulse oximeters typically utilize a non-invasive sensor that transmits light through a patient's tissue and that photoelectrically detects the absorption of the transmitted light in such tissue. Such techniques, however, may not fully leverage the information that may be acquired. In particular, while analyses based on light absorption may provide useful measurements, other information that is not based on absorption of light in the tissue may be uncollected and unused, thereby depriving a caregiver of potentially useful information.

BRIEF DESCRIPTION OF THE DRAWINGS

Advantages of the disclosed techniques may become apparent upon reading the following detailed description and upon reference to the drawings in which.

DETAILED DESCRIPTION OF SPECIFIC EMBODIMENTS

Figure 1:
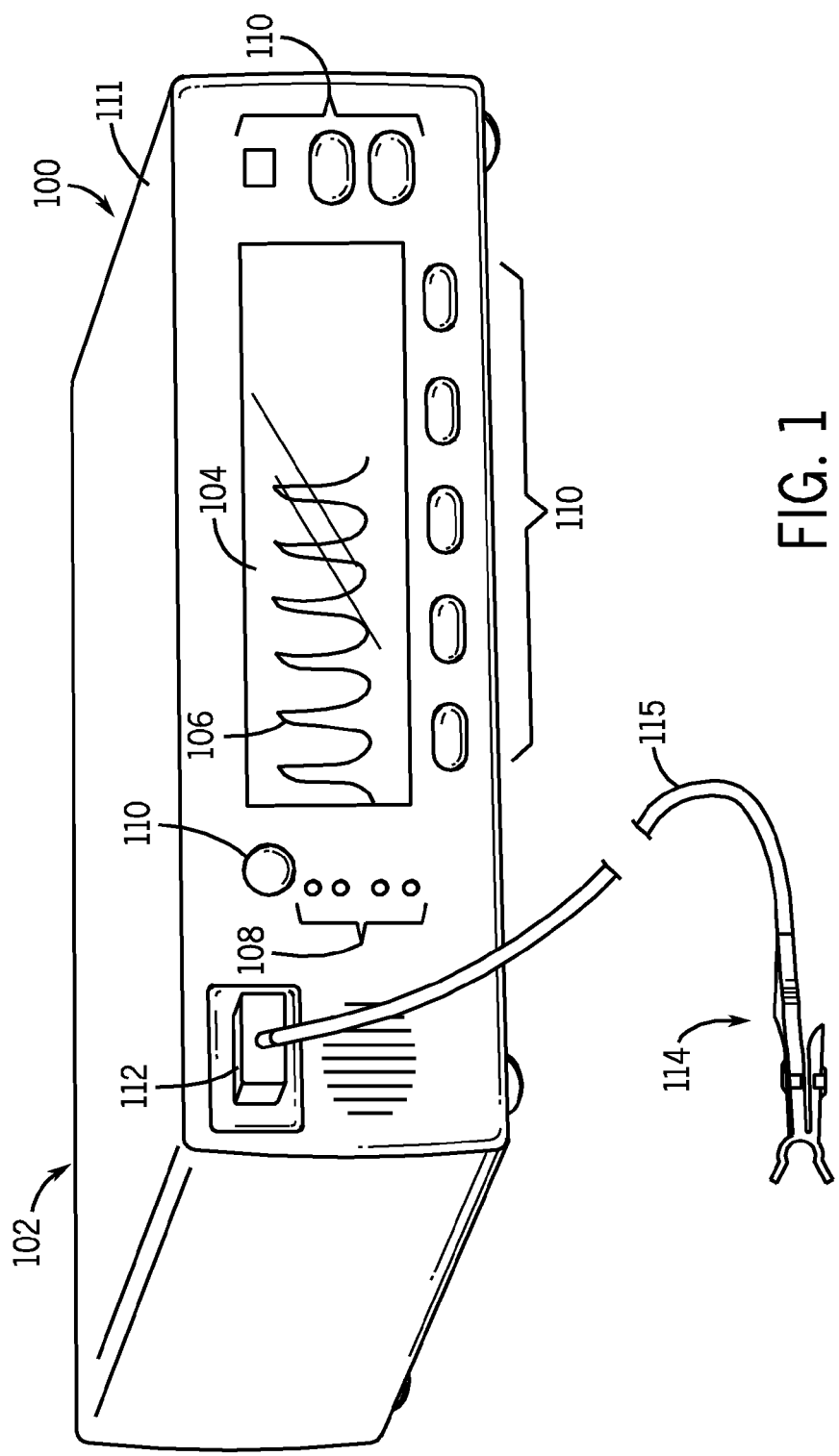
FIG. 1 illustrates a perspective view of a pulse oximeter in accordance with an embodiment.

One or more specific embodiments of the present techniques will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Present embodiments relate to measuring physiologic parameters corresponding to blood flow in a patient by emitting into the patient's tissue light that is modulated to generate photon density waves, detecting the light after it has passed through the patient's tissue, and processing a signal generated in response to the detected light using wavelet transforms to identify physiological information. More specifically, the signal generated in response to the detected light may contain phase and amplitude information of the photon density waves that are transmitted towards the patient's tissue and scattered and absorbed by hemoglobin in the tissue. This signal, referred to herein as the PDW signal, may be processed using wavelet analysis, such that the phase and amplitude information may be analyzed in both frequency and time domains. Various physiological parameters may be determined based on the time-frequency analyses of the transformed PDW signal.

Photon density waves may be described as progressively decaying waves of intensity. Photons generated by a light source generally make random migrations in a scattering medium, and may, at a given modulation frequency, collectively form a photon density wave that moves away from the light source. Photon propagation is generally dictated by scattering and absorption in the medium through which the waves are moving. Like other waves, photon density waves undergo refraction, diffraction, interference, dispersion, attenuation, and so forth. The photons of the photon density wave may propagate through the medium (i.e., the tissue) to be detected at a photodector, and the phase changes and amplitude changes of the detected waves may facilitate measurement of changes in the total scattering particles as well as the absorber concentration. The phase of the detected waves may be used to determine photon scattering while the amplitude of such waves may indicate the absorption of photons by the tissue.

In particular, changes in phase of a PDW signal may correspond to a total number of scattering particles (e.g., total hemoglobin) in the observed medium. For example, since the scattering coefficient of the tissue may change depending on the total number of hemoglobin particles in the tissue, variations in the phase changes may correspond to variations in the total hemoglobin in the tissue. Thus, changes in the phase of a PDW signal may be predominately due to the total number of scattering hemoglobin particles, rather than to the ratio of different particles (e.g., oxygenated and deoxygenated hemoglobin) in the tissue.

On the other hand, changes in the amplitude of the photon density waves may correspond to the absorption of specific light frequencies (e.g. red or infrared light) in the observed volume, and, thus, a ratio of different types of particles in the probed medium. Oxygenated and deoxygenated hemoglobin particles may both scatter the photons of modulated photon density waves, but may absorb different frequencies of light. By analyzing the changes in amplitude in the PDW signal, a ratio of different types of particles in the tissue may be estimated. Data acquired using photon density waves may thus provide additional physiological information to what is typically provided in a pulse oximetry signal.

When the photon density waves transmitted and/or scattered through the tissue are received at a detector in the pulse oximeter, the detector (e.g., a photodiode) may produce a current proportional to the intensities of the received photon density waves. The produced current may be processed to determine certain physiological characteristics. In some pulse oximetry systems, Fourier analysis may be used to process the signal. Fourier transforms, however, may return a globally averaged energy value without information regarding the temporal location of signal components. Therefore, in one or more embodiments of the present disclosure, wavelet transforms may instead be used for processing and analyzing the signal generated in response to the photon density waves. One advantage that may be provided by the use of wavelet transforms is that wavelet transforms may allow a signal to be decomposed such that the frequency characteristics may be analyzed with respect to the temporal location of the frequency characteristics in a PDW signal.

Furthermore, as the PDW signal is obtained by emitting photon density waves into tissue, the PDW signal may contain information regarding both the absorption (e.g., amplitude) and scattering (e.g., phase) of the measured tissue. Thus, wavelet transforms may be used to identify differences between the absorption and scattering of the photon density waves by the tissue, and may enable an analysis of such wave characteristics with respect to time and frequency. As will be further discussed, wavelet analysis of PDW signals may enable a pulse oximeter to determine whether signal changes result from physiological changes or non-physiological interferences, and may also enable the detection of certain physiological conditions. For example, in one embodiment, wavelet analysis may enable a pulse oximeter to determine whether absorption and scattering are temporally correlated, and may determine that changes in absorption may be due to non-physiological interferences (e.g., motion) rather than physiological changes based on this temporal correlation. Thus, if changes in observed amplitude (e.g., the absorption of oxygenated or deoxygenated hemoglobin) do not correlate with a corresponding change in phase (e.g., scattering of total hemoglobin particles in tissue), the observed changes in absorption may be attributed to patient motion as opposed to changes in the physiological parameter being measured. In some embodiments, non-physiological signal components (e.g., patient motion) may be removed from the PDW signal to improve the accuracy of physiological data calculated from the PDW signal.

Turning to FIG. 1, a perspective view of a medical device is illustrated in accordance with an embodiment. The medical device may be a pulse oximeter 100. The pulse oximeter 100 may include a monitor 102, such as those available from Nellcor Puritan Bennett LLC. The pulse oximeter 100 may be utilized to observe the blood constituents of a patient's arterial blood to facilitate estimation of the state of oxygen exchange in the patient's body by emitting light into tissue and detecting the light after dispersion and/or reflection by the tissue. The amount of light that passes through the tissue and other characteristics of the light may vary in accordance with the changing amount of certain blood constituents in the tissue and the related light absorption and/or scattering. As with conventional pulse oximeter systems, the pulse oximeter 100 may emit light from two or more LEDs or lasers into pulsatile tissue and then detect the transmitted light with a light detector (e.g., a photodiode or photo-detector) after the light has passed through the pulsatile tissue. Such measurements may be utilized to estimate a percentage of blood oxygen saturation in the probed volume of blood. Additionally, in one embodiment, the pulse oximeter 100 may modulate the emitted light to generate photon density waves at a high frequency to detect phase shifts that correlate predominantly to scattering particles in the probed volume of blood.

The monitor 102 may be configured to display calculated parameters on a display 104. As illustrated in FIG. 1, the display 104 may be integrated into the monitor 102. However, the monitor 102 may also be configured to provide data via a port to an external display or secondary monitor. The display 104 may be configured to display computed physiological data including, for example, an oxygen saturation percentage, a pulse rate, and/or a plethysmographic waveform 106. The oxygen saturation percentage may be a functional arterial hemoglobin oxygen saturation measurement in units of percentage $SpO_2$, while the pulse rate may indicate a patient's pulse rate in beats per minute. The monitor 102 may also display information related to alarms, monitor settings, and/or signal quality via indicator lights 108.

To facilitate user input, the monitor 102 may include a plurality of control inputs 110. The control inputs 110 may include fixed function keys, programmable function keys, and soft keys. Specifically, the control inputs 110 may correspond to soft key icons in the display 104. Pressing control inputs 110 associated with, or adjacent to, an icon in the display may select a corresponding option. The monitor 102 may also include a casing 111. The casing 111 may aid in the protection of the internal elements of the monitor 102 from damage.

The monitor 102 may further include a sensor port 112. The sensor port 112 may allow for connection to an external sensor 114, via a cable 115 which connects to the sensor port 112. The sensor 114 may be of a disposable or a non-disposable type. Furthermore, the sensor 114 may be used to obtain readings from a patient, which can be used by the monitor to calculate certain physiological characteristics such as the blood-oxygen saturation of hemoglobin in arterial blood, the volume of individual blood pulsations supplying the tissue, and/or the rate of blood pulsations corresponding to each heartbeat of a patient.

Figure 2:
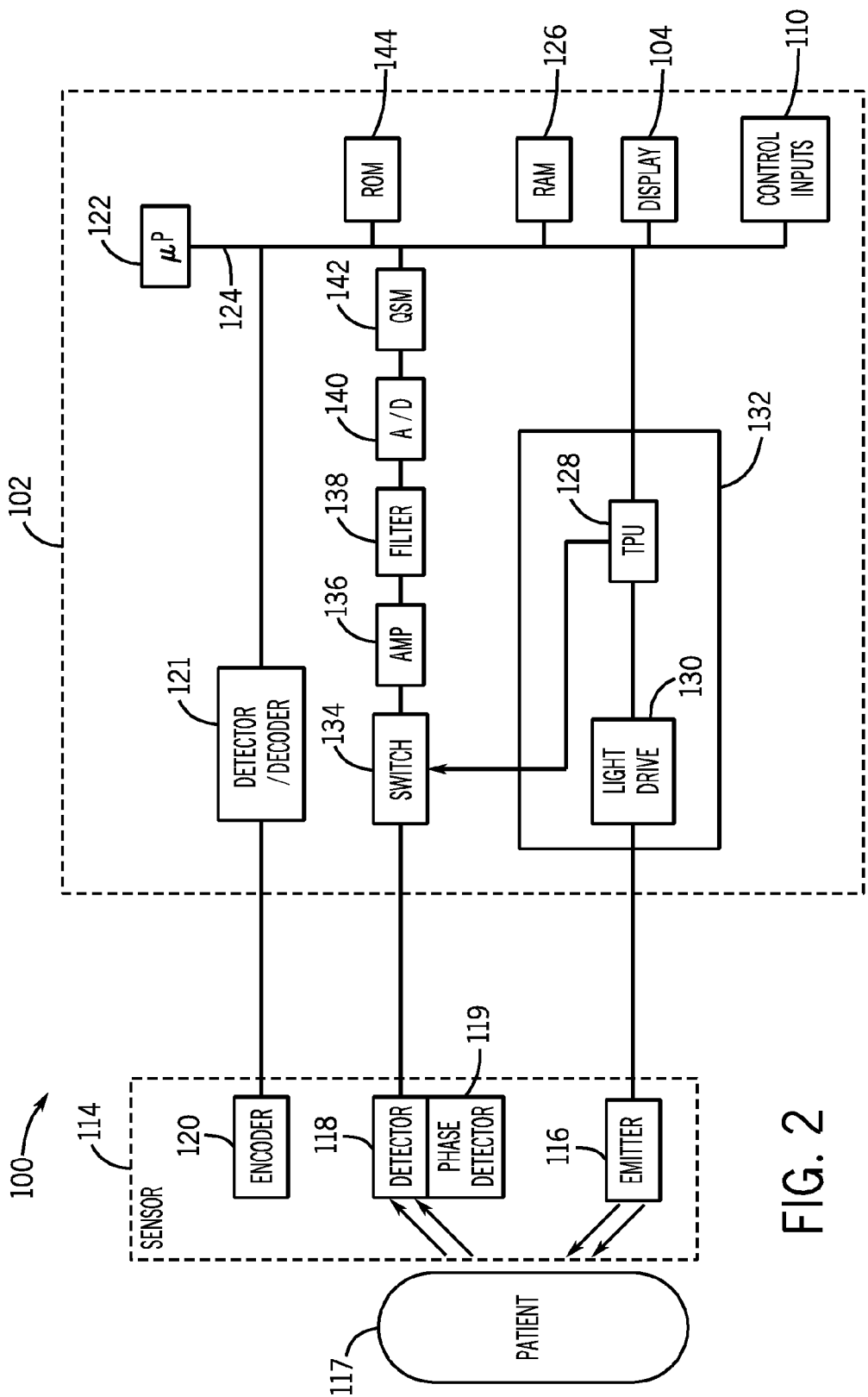
FIG. 2 illustrates a simplified block diagram of a pulse oximeter, according to an embodiment.

Turning to FIG. 2, a simplified block diagram of a pulse oximeter system 100 is illustrated in accordance with an embodiment. Specifically, certain components of the sensor 114 and the monitor 102 are illustrated in FIG. 2. The sensor 114 may include an emitter 116, a detector 118, and an encoder 120. The emitter 116 may receive modulated drive signals from the monitor 102, and may activate and deactivate a light emitting device at certain intervals. Thus, the monitor 102 may activate and deactivate the light emitted by the emitter 116 at high frequencies to generate photon density waves. The photon density waves may facilitate measurements relating to scattering in the probed medium based on phase changes in the emitted photon density waves.

The emitter 116 may be capable of emitting one or more wavelengths of light, e.g., RED and infrared (IR) light, into the tissue of a patient 117, where the RED wavelength may be between about 600 nm and about 700 nm, and the IR wavelength may be between about 800 nm and about 1000 mm. The emitter 116 may include a single emitting device, for example, with two light emitting diodes (LEDs) or the emitter 116 may include a plurality of emitting devices with, for example, multiple LED's at various locations. Regardless of the number of light emitting devices, the emitter 116 may be used to measure, for example, blood oxygen saturation, water fractions, hematocrit, or other physiologic parameters of the patient 117, as discussed herein. It should be understood that, as used herein, the term "light" may refer to one or more of radio, microwave, millimeter wave, infrared, visible, ultraviolet, gamma ray or X-ray electromagnetic radiation, and may also include any wavelength within the radio, microwave, infrared, visible, ultraviolet, or X-ray spectra, and that any suitable wavelength of light may be appropriate for use with the present disclosure. Further, in one or more embodiments, the light may refer to photon density waves, or light emitted in response to modulated drive signals.

In one embodiment, the detector 118 may be an array of detector elements that may be capable of detecting light at various intensities and wavelengths. In operation, light enters the detector 118 after passing through the tissue of the patient 117. The detector 118 may convert the light at a given intensity, which may be directly related to the absorbance and/or reflectance of light in the tissue of the patient 117, into an electrical signal. That is, when more light at a certain wavelength is absorbed or reflected, less light of that wavelength is typically received from the tissue by the detector 118. For example, the detector 118 may include one or more photodiodes, or any other element capable of generating a current or voltage in response to the light incident on the detector 118. After converting the received light to an electrical signal, the detector 118 may send the signal to the monitor 102, where physiological characteristics may be calculated based at least in part on the absorption of light in the tissue of the patient 117.

In some embodiments, in addition to the emitter 116 and the detector 118, the sensor 114 may also contain various other features. For example, the sensor 114 may include a phase detector 119 capable of detecting phase shifts in photon density waves observed by the detector 118. While the phase detection feature 119 is positioned within the sensor 114 in the illustrated embodiment, in other embodiments, the phase detection feature 119 may also be located within the monitor 102.

Additionally the sensor 114 may include an encoder 120, which may contain information about the sensor 114, such as what type of sensor it is (e.g., whether the sensor is intended for placement on a forehead or digit) and the wavelengths of light emitted by the emitter 116. This information may allow the monitor 102 to select appropriate algorithms and/or calibration coefficients for calculating the patient's 117 physiological characteristics. The encoder 120 may, for instance, be a memory on which one or more of the following information may be stored for communication to the monitor 102: the type of the sensor 114; the wavelengths of light emitted by the emitter 116; and the proper calibration coefficients and/or algorithms to be used for calculating the patient's 117 physiological characteristics. In one embodiment, the data or signal from the encoder 120 may be decoded by a detector/decoder 121 in the monitor 102.

Signals from the detector 118 and the encoder 120 may be transmitted to the monitor 102. The monitor 102 may include one or more processors 122 coupled to an internal bus 124. Also connected to the bus 124 may be a RAM memory 126 and a display 104. The monitor 102 may also include a modulator 132, which may include a time processing unit (TPU) 128 and light drive circuitry 130. The modulator 132 may modulate the drive signals that activate the LEDs or other emitting structures of the emitter 116. The modulator 132 may be hardware-based, a software-based, or some combination thereof. For example, a software aspect of the modulator 132 may be stored on the memory 126 and may be controlled by the processor 122. The TPU 128 may include a sine wave generator, and may provide timing control signals to light drive circuitry 130, which controls when the emitter 116 is activated, and if multiple light sources are used, the multiplexed timing for the different light sources. TPU 128 may also control the gating-in of signals from detector 118 through a switching circuit 134. These signals are sampled at the proper time, depending at least in part upon which of multiple light sources is activated, if multiple light sources are used.

The modulator 132 may be configured to modulate light emitting devices in the emitter 116 at sufficiently high frequencies (e.g., approximately 50 MHz to 3.0 GHz) to generate resolvable photon density waves to propagate through the tissue of the patient 117. While a traditional pulse oximeter may conduct measurements at low frequencies (e.g., 1.5 KHz) to return a DC signal, in some embodiments, the modulator 132 may be configured to modulate between 100 MHz and 1 GHz or between 600 MHz and 1 GHz, for example. While the modulator 132 is depicted as in the monitor 102, in some embodiments, the modulation function may be performed by a modulator disposed in the sensor 114. In one embodiment, the modulation and detection features may both be located within the sensor 114 to reduce the distance traveled by the signals, and to reduce potential interferences.

The received signal from the detector 118 may be processed to provide certain physiological data. In one embodiment, the received signal may be passed through an amplifier 136, a low pass filter 138, and an analog-to-digital converter (ADC) 140 for amplifying, filtering, and digitizing the electrical signals the from the sensor 114. The digital data may then be stored in a queued serial module (QSM) 142, for later downloading to RAM 126 as QSM 142 fills up. There may also be multiple parallel paths for separate amplifiers, filters, and A/D converters for multiple light wavelengths or spectra received. Further, the processor 122 may calculate the oxygen saturation or some other physiological parameter of interest based on the received signals corresponding to the light received by the detector 118. For example, the processor may execute instructions or algorithms stored on the memory 144, and may be configured to perform calculations to determine a value related to the quantity of scattering particles in the probed tissue.

As discussed, the pulse oximeter 100 may emit and detect light waves to facilitate non-invasive measurement of a patient's physiological characteristics. In embodiments, the pulse oximeter 100 may generate resolvable photon density waves and identify physiological and/or non-physiological signal components of PDW signal detected after the photon density waves have passed through a medium (e.g., a patient's tissue). The wave characteristics used to analyze the PDW signal and identify signal components may include characteristics relating to the absorption of the light at the emitted wavelengths in the probed medium (e.g., amplitude change) and characteristics relating predominantly to scattering in the probed medium (e.g., phase shift).

The correlation between certain wave characteristic (e.g., amplitude and phase) and certain medium characteristics (e.g., absorption and scattering) may be based on the high frequency modulation of the light emitted by the pulse oximeter 100, which generate the resolvable photon density waves. In some embodiments, the pulse oximeter 100 may emit light that is modulated at a high frequency (e.g., 50 MHz to 3.0 GHz), and then measure the phase shift of these high frequency waves to facilitate estimation of a total number of scattering particles in the observed medium. Similarly, the pulse oximeter 100 may be utilized to measure wave characteristics that relate predominantly to absorption in an observed volume. For example, the pulse oximeter 100 may detect changes in AC and DC amplitudes of the resolvable photon density waves to facilitate detection of a ratio of certain constituents in the blood (e.g., a ratio of oxygenated to deoxygenated hemoglobin).

Figure 3:
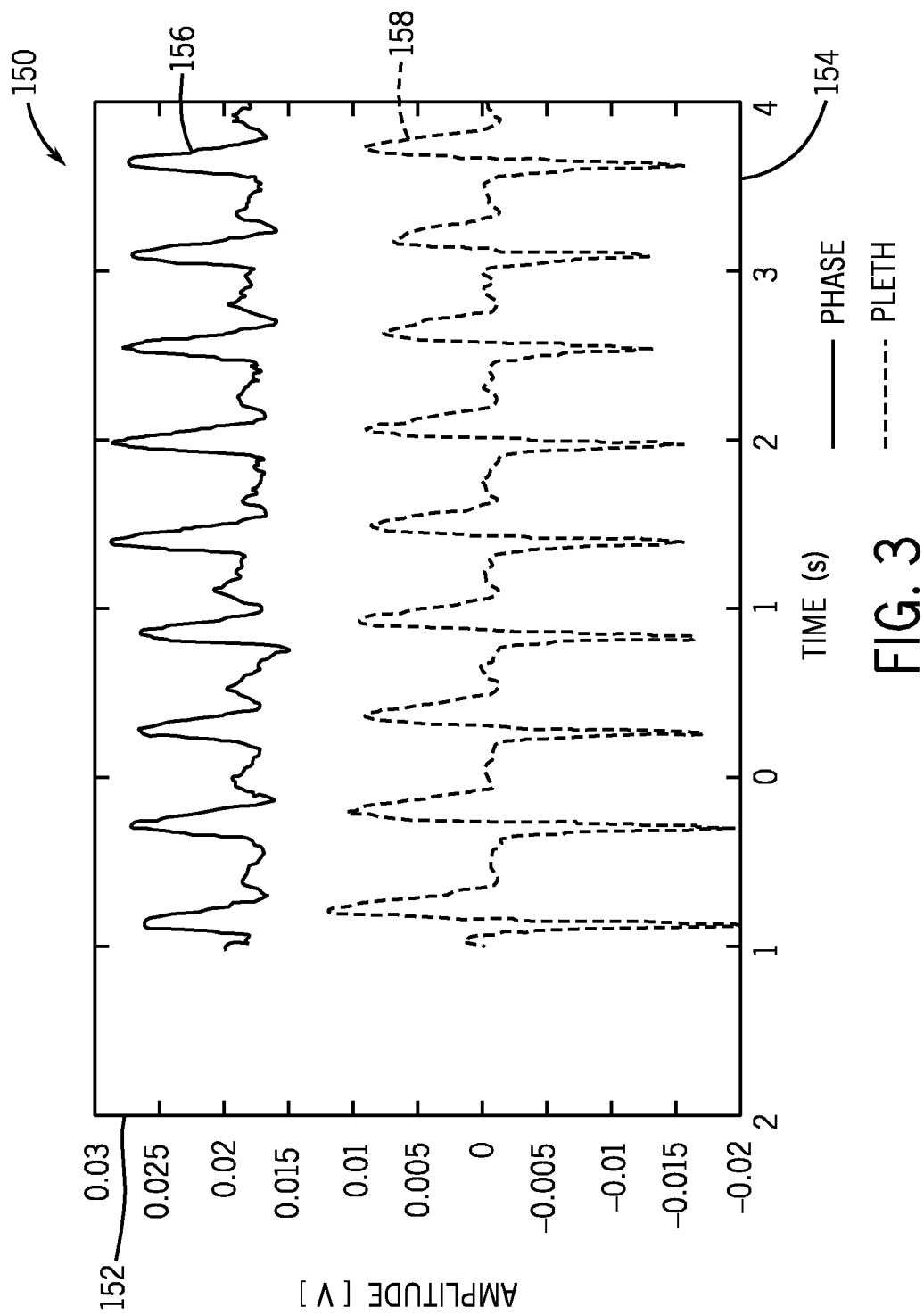
FIG. 3 is a graph depicting time-based phase and photoplethysmography (pleth) signals acquired using a photon density wave pulse oximeter, according to an embodiment.

The graph 150 of FIG. 3, depicts the amplitude 152 over time 154 of a phase signal 156 and a plethysmographic (pleth) signal 158 from a pulse oximeter 100 (as in FIGS. 1 and 2). The phase signal 156 and the pleth signal 158 may also each be derived from a respective PDW signal, as discussed above. In one embodiment, a sensor 114 of the pulse oximeter 100 may be configured to modulate emitted light to generate photon density waves, and may detect waves containing both phase and amplitude data (e.g., the phase signal 156 and the pleth signal 158).

The phase signal 156 may vary proportionally to the intensity of light received at the detector 118 having a phase change from the emitted photon density wave. As discussed, the phase change characteristic of the received light may indicate a total number of particles (e.g., total hemoglobin), as the scattering coefficient in the medium (e.g., the tissue) may vary proportionally with the variation of total hemoglobin in the tissue. The pleth signal 158 may vary proportionally to the intensity of light received at the detector 118. As different particles in the tissue may absorb different wavelengths of light, the intensity of light received at the detector 118 may indicate a ratio of different types of particles in the tissue (e.g., deoxygenated or oxygenated hemoglobin).

Each of the phase signal 156 and pleth signal 158 may be processed to enable the identification of certain physiological parameters of the patient 117. In one embodiment, a pulse oximeter 100 that is capable of generating photon density waves and receiving/detecting the returns may use wavelet transforms to process the returned signal. For example continuous wavelet transforms may be applied to the PDW signals. In some embodiments, the PDW signals may also be digitized, such that discrete or complex wavelet transforms may be applied.

Using continuous wavelet transformation in one example, the detector 118 may produce a phase signal 156 and a pleth signal 158 in response to the received light. Wavelet transforms may be applied to produce an energy map having both time and frequency information. In one embodiment, algorithms or instructions may be implemented or performed by the monitor 102 (e.g., by the processor 122) to transform PDW signals, such that the signals may be analyzed with respect to time, frequency, and/or magnitude. For example, the wavelet transform of a signal x(t) may be defined in the equation below:

$$T(a, b) = \frac{1}{\sqrt{a}} \int_{-\infty}^{+\infty} x(t)\psi^*\left(\frac{t-b}{a}\right) dt \qquad \text{eq. (1)}$$

In eq. (1), $\psi^*(t)$ is the complex conjugate of the wavelet function $\psi(t)$. The variable a is the dilation parameter of the wavelet, and b is the location parameter of the wavelet. In one or more embodiments, any suitable wavelet function, including a Morelet wavelet, may be used to obtain a time-frequency representation of the PDW signals (e.g., the phase signal 156 and the pleth signal 158). The transform of eq. (1) may be regarded as a time-frequency representation where the characteristic frequency associated with the wavelet is inversely proportional to the scale a, and can be used to construct a representation of a signal on a transform surface. The energy density function of the wavelet transform, also referred to as the scalogram, may be defined by the equation below:

$$S_R(a, b) = \frac{|T(a, b)|^2}{a} \qquad \text{eq. (2)}$$

where "| |" is the modulus operator. Thus, by applying the wavelet transform on a time-based signal for the time-frequency representation of the signal, and then applying the energy density function of the wavelet transform, a scalogram may be produced. The scalogram, which may also be interpreted as a spectral density of frequency over time, may be a three dimensional model (having time, frequency, and magnitude) from which certain physiological information may be obtained. A comparison of a time-based phase signal (e.g., phase signal 156 in FIG. 3) and its corresponding scalogram are presented in FIGS. 4 and 5.

Figure 4:
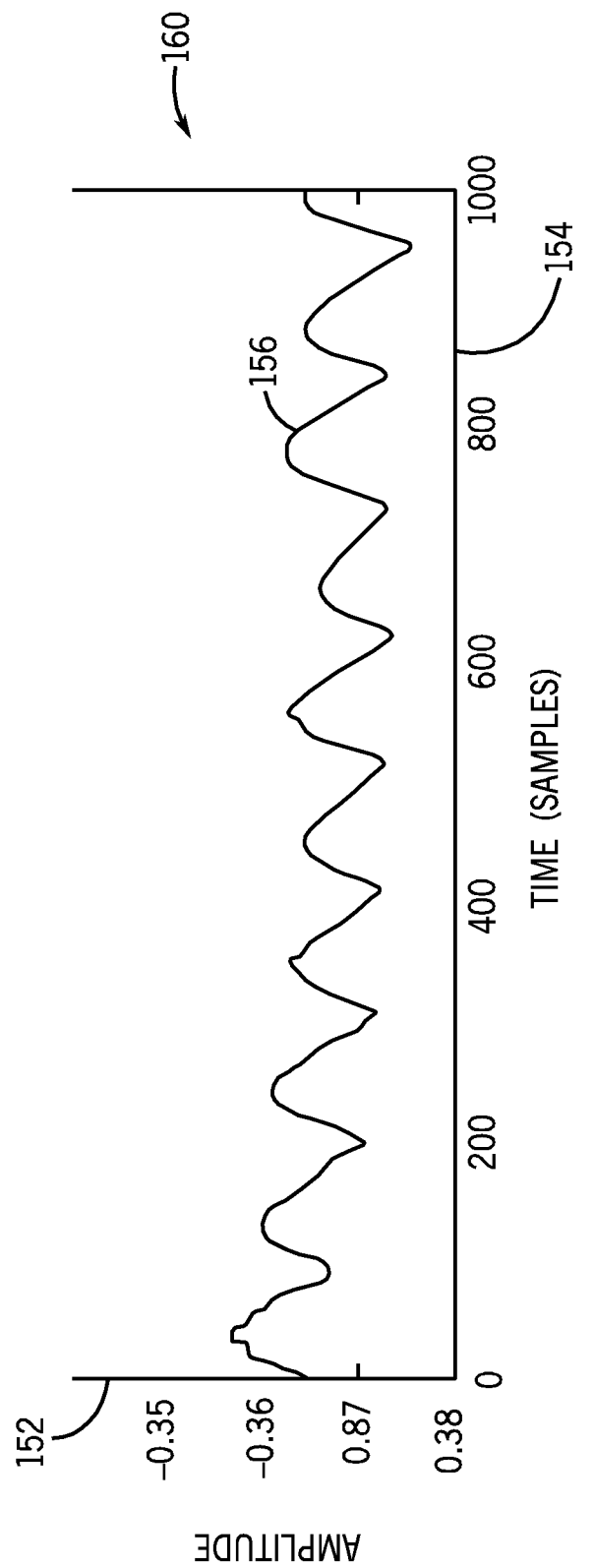
FIGS. 4 and 5 depict, respectively, a graph of a phase signal and a corresponding scalogram resulting from a wavelet transformation of the phase signal, according to an embodiment.

In FIG. 4, the graph 160 displays a time-based phase signal 156, which changes in amplitude 152 over time 154. As discussed, generating and emitting photon density waves and receiving the photon density waves that are transmitted and/or scattered through the tissue may result in additional phase information, such as the phase signal 156, which may not be available using a typical unmodulated light source. In one embodiment, light modulated at high frequencies (e.g., 50 MHz to 3 GHz) generate resolvable photon density waves from which phase changes may be detected. The variations in scattering hemoglobin particles that may occur with each cardiac cycle correspond with variations in phase change, as depicted in the variations in amplitude 152 of the phase signal 156 in the graph 160.

Figure 5:
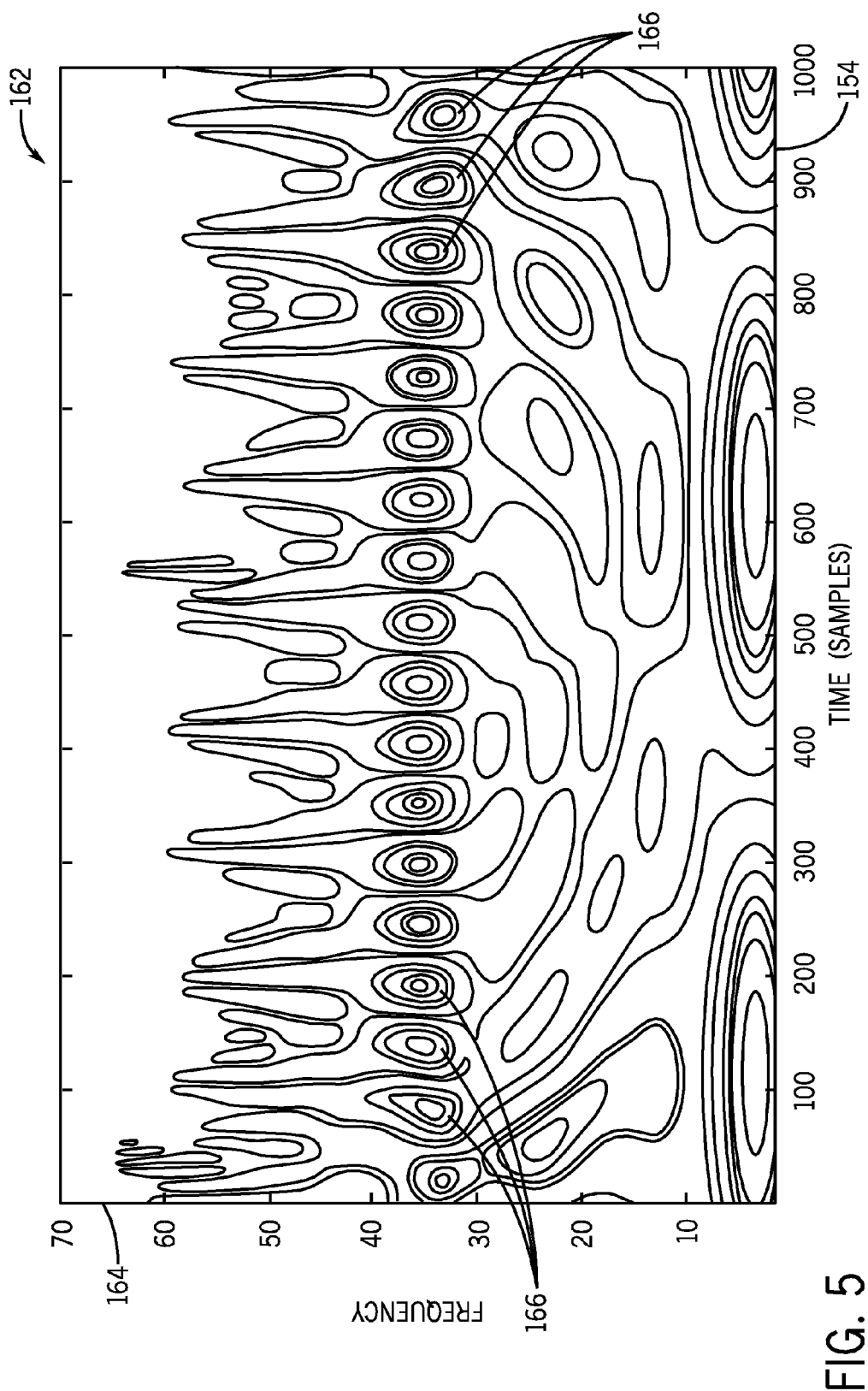

In addition to the phase information which may be received by using photon density waves in a pulse oximeter 100, wavelet transformations may provide further information by enabling the analyses of phase information in both the time and frequency domains. The scalogram 162 in FIG. 5 provides a time-frequency representation of the phase signal 156. The phase signal 156 and the time-frequency representation of the signal 156 may be represented over the same time 154 in the graph 160 and the scalogram 162. The scalogram 162 may provide a relationship between frequency 164 and amplitude, which may be depicted as a spectral density in the scalogram 162. Different features may be seen at different frequencies of the transformed signal 156, and may match temporally with the original time-based signal 156. For example, the features 166 may correspond to some physiological parameter (e.g., oxygen saturation, pulse rate, breathing rate, etc.) within a frequency band of the wavelet-transformed signal 156.

Variations in the spectral density of the scalogram 162 may be based on the changes in the amplitude of the phase, or changes in the total number of hemoglobin. Patterns and ridges in the scalogram 162 may be the locus of points of local maxima in the plane, and may provide information concerning the location of temporal features, including the instantaneous frequency of the signal at that temporal location. Thus, both the magnitude of phase change, as well as the instantaneous frequency of phase change, may be available for any temporal location of the scalogram 162. As some transformations (e.g., a typical Fourier transformation) may return a globally averaged energy value without information regarding the temporal location of signal components, the temporal location of certain phase signal characteristics may not be available. Thus, applying wavelet transforms may be particularly useful in identifying certain non-physiological signal components (e.g., peaks or spikes) within the phase signal 156.

Figure 6:
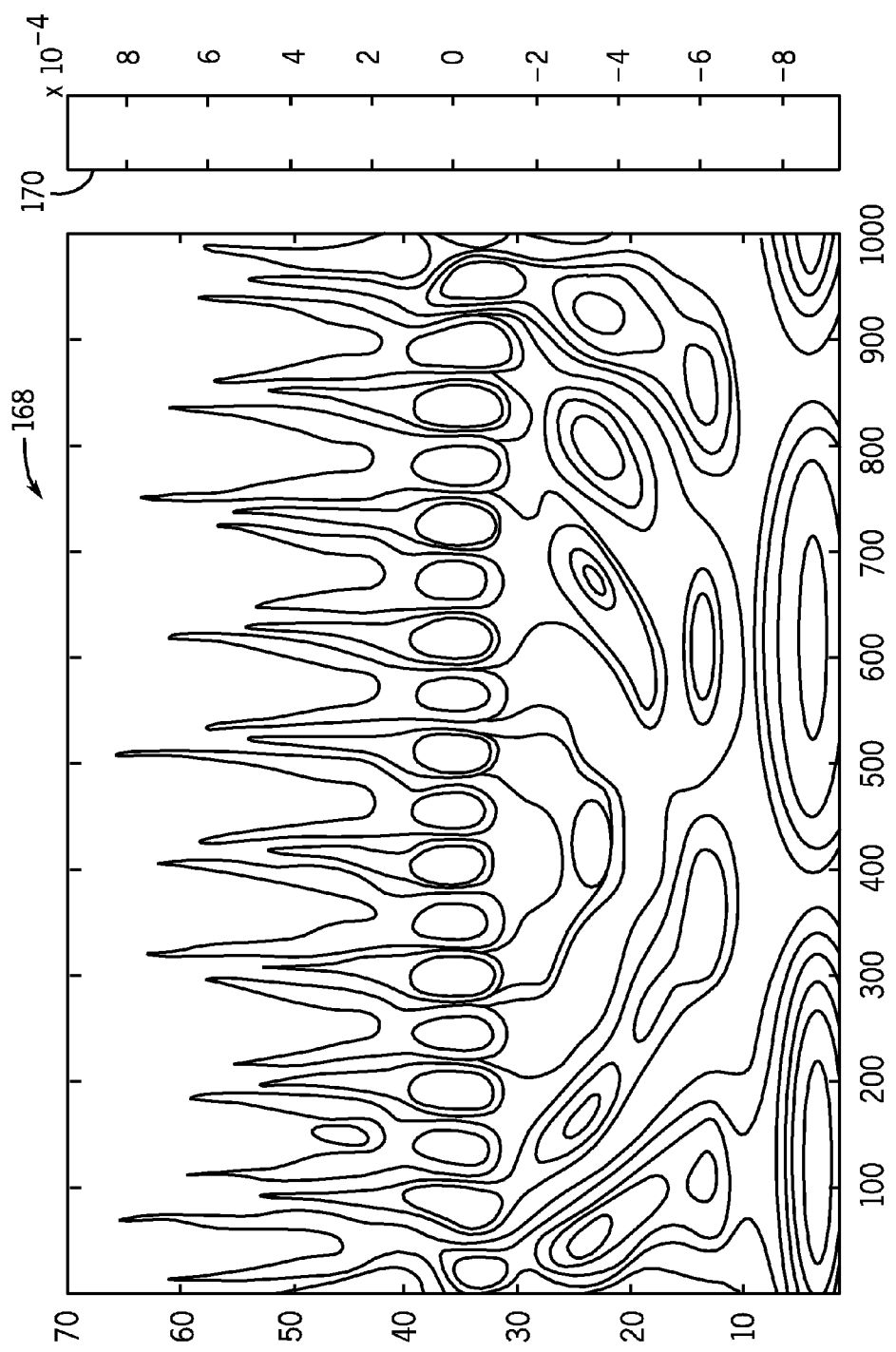
FIG. 6 depicts an analysis of a scalogram based on an intensity scale, according to an embodiment.

As discussed with respect to eq. (1), the characteristic frequency associated with the wavelet is inversely proportional to the scale a. The scalogram 168 of FIG. 6 inverts the magnitudes of the scalogram 162, and scalogram features may be analyzed with respect to its spectral density. The scale 170 represents how the spectral density may be determined for the scalogram 168.

Figure 7:
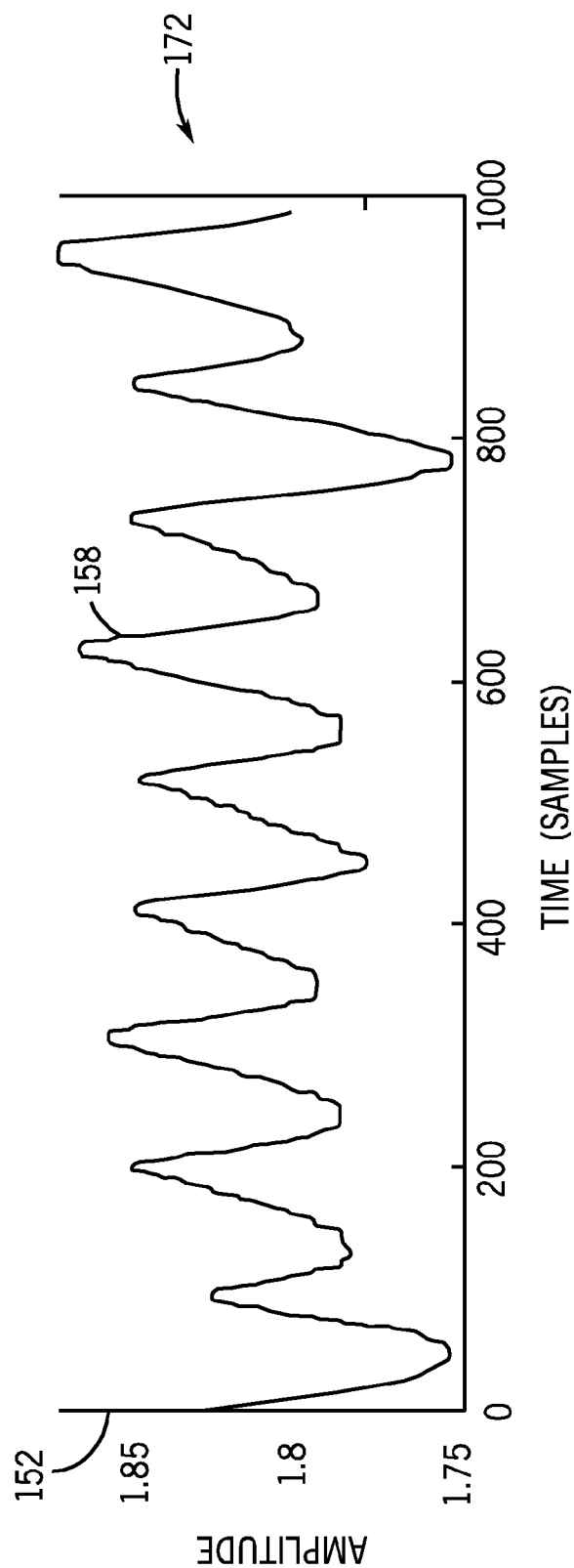
FIGS. 7 and 8 depict, respectively, a graph of a pleth signal and a corresponding scalogram resulting from a wavelet transformation of the pleth signal, according to an embodiment.
Figure 8:
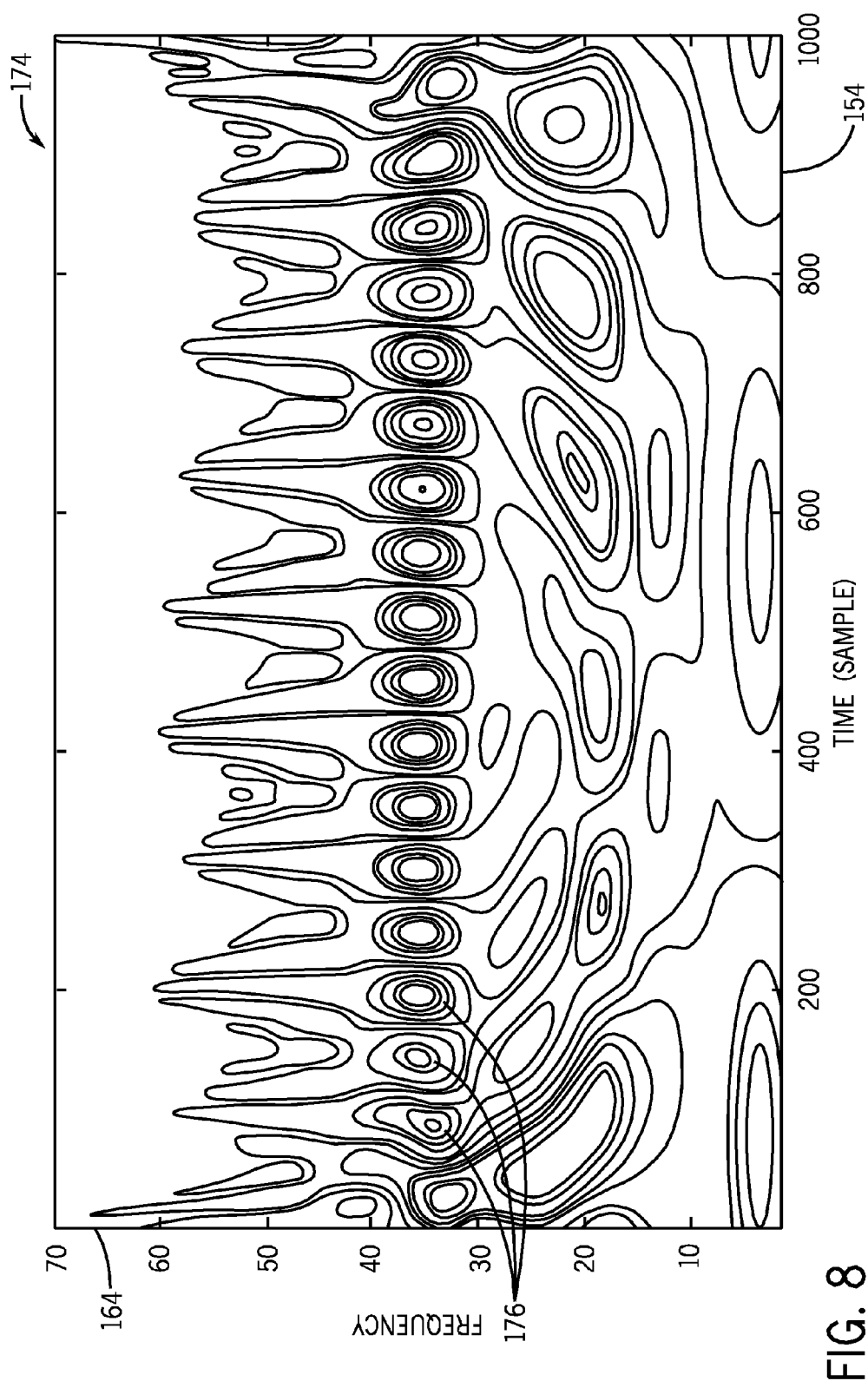

A comparison of the time-based signal of a pleth signal (e.g., pleth signal 158 in FIG. 3) and its corresponding scalogram are presented in FIGS. 7 and 8. In FIG. 7, the graph 172 displays a time-based pleth signal 158, which changes in amplitude 152 over time 154. The corresponding pleth signal scalogram 174 in FIG. 8 provides a time-frequency representation of the pleth signal 158. The pleth signal 158 and the time-frequency representation of the signal 158 may have the same time scale 154 in the graph 172 and the scalogram 174. In addition, the pleth signal scalogram 174 may provide a relationship between frequency 164 and magnitude of the pleth signal 158. As discussed with respect to the phase signal 156 and the corresponding phase signal scalogram 162 of FIGS. 4 and 5, the magnitude of the pleth signal scalogram 174 may be represented in varying spectral density, from which features 176 may be detected. The varying spectral density may correlate to variations in the amplitude of the pleth signal 158, which may be proportional to the variation of photons absorbed by certain hemoglobins (e.g., oxygenated or deoxygenated hemoglobin). Further, the time-frequency representation provided by the scalogram 174 may facilitate identifying and/or removing non-physiological signal components, and in some embodiments, the scalogram 174 may facilitate in determining certain physiological parameters.

Furthermore, in some embodiments, the phase signal scalogram 162 and the pleth signal scalogram 174 may be compared or analyzed with respect to one another to determine certain physiological parameters. For example, an increase in frequency or amplitude at one temporal location may be detected on a pleth signal scalogram 174, possibly indicating a change in the number of photon absorbing hemoglobin. The phase signal scalogram 162 may be analyzed at the same temporal location to determine whether the change in photon absorption corresponds to a change in hemoglobin ratio (e.g., the ratio between oxygenated and deoxygenated hemoglobin), and/or a change in total hemoglobin.

Figure 9:
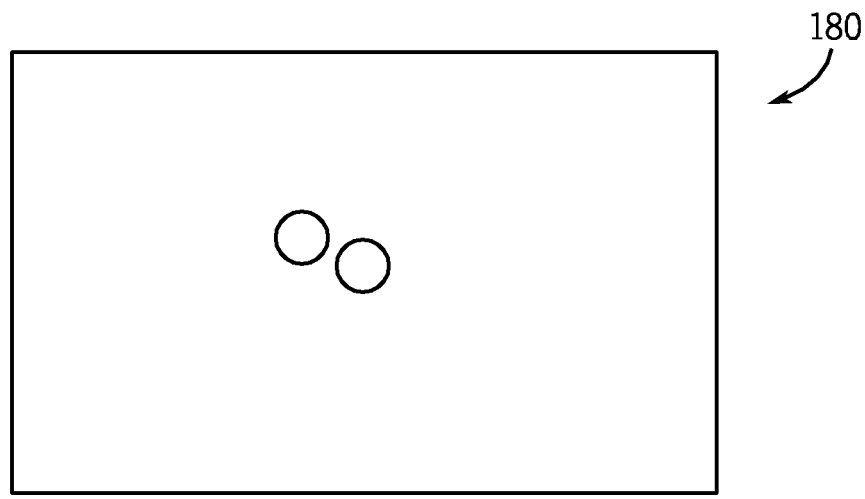
FIGS. 9-11 illustrate a method of comparing a pattern with an image and using a threshold detection method to detect instances of the pattern, according to an embodiment.
Figure 10:
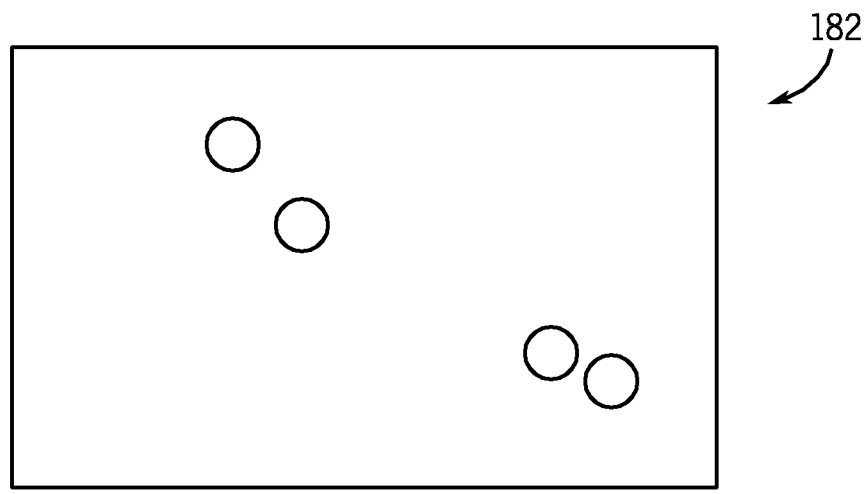
Figure 11:
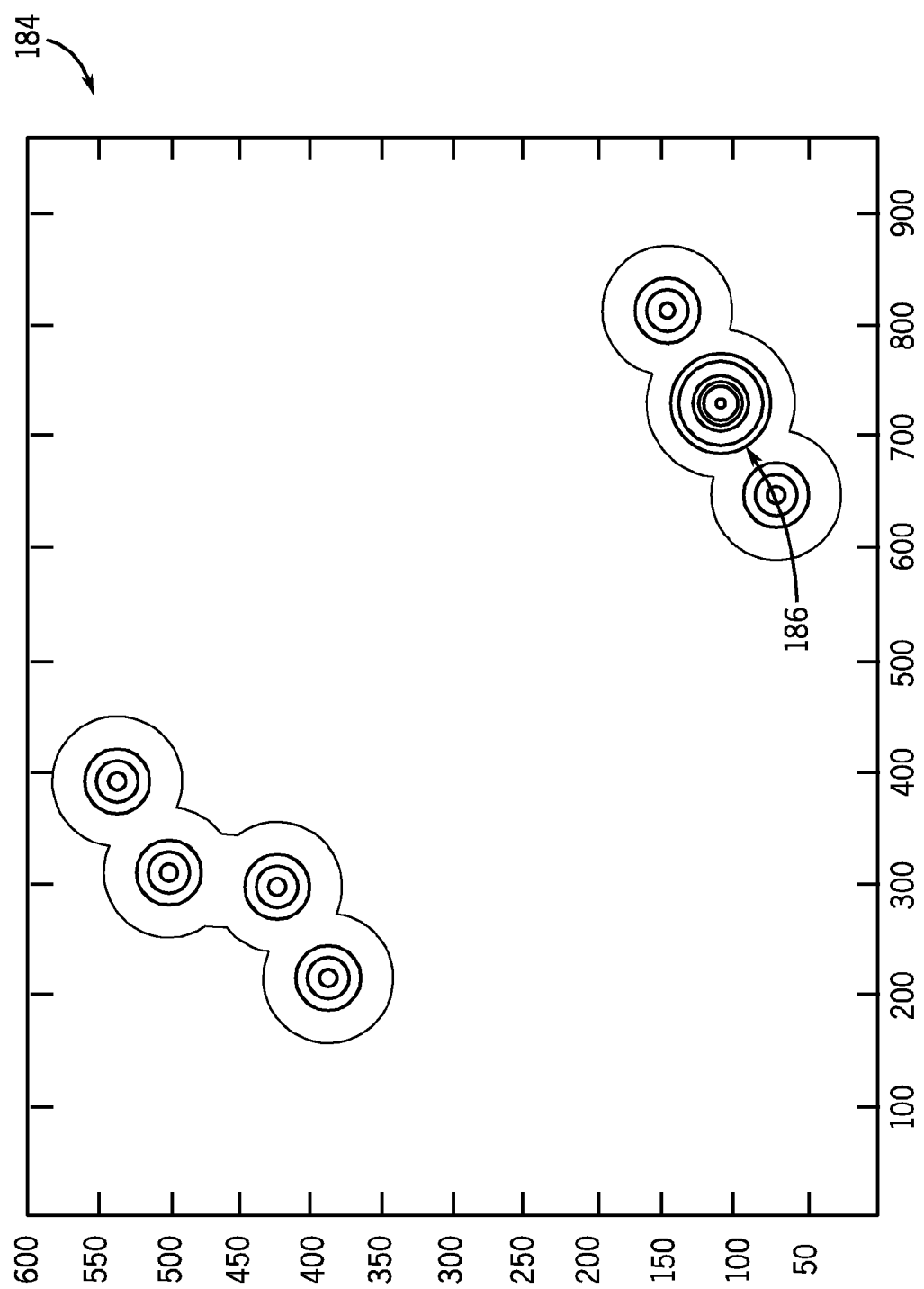

As certain features in a scalogram may indicate certain physiological conditions, the present techniques may also include methods of determining the presence of patterns in a scalogram which may, due to their repeated or repetitive nature, indicate a physiological condition. That is, ongoing or repeated physiological conditions may be characterized by discernible and repeatable patterns, whereas noise, motion artifacts, and other non-repetitive phenomena cannot typically be characterized by a recurring pattern or signature. FIGS. 9-11 depict one example of how a pattern indicative of a physiological condition may be detected in a scalogram. In one embodiment, a pattern of interest 180 depicted in FIG. 9 may be known to indicate a certain physiological condition. The image 182 of FIG. 10 may represent some portion of a scalogram. Some embodiments may include a method of determining whether the pattern of interest 180 is present in the image 182 by cross correlating the pattern 180 with the image 182. The resulting image 184 of FIG. 11 may represent the cross correlation. The identification of the pattern 180 may include setting a threshold to identify the pattern 180. For example, the threshold may be some spectral intensity, and instances in the image 182 that exceed a threshold intensity may indicate that the pattern 180 is present in the image 182. For example, the presence of the depicted brighter spot 186 may be used to identify the pattern 180 in the example image 182.

Figure 12:
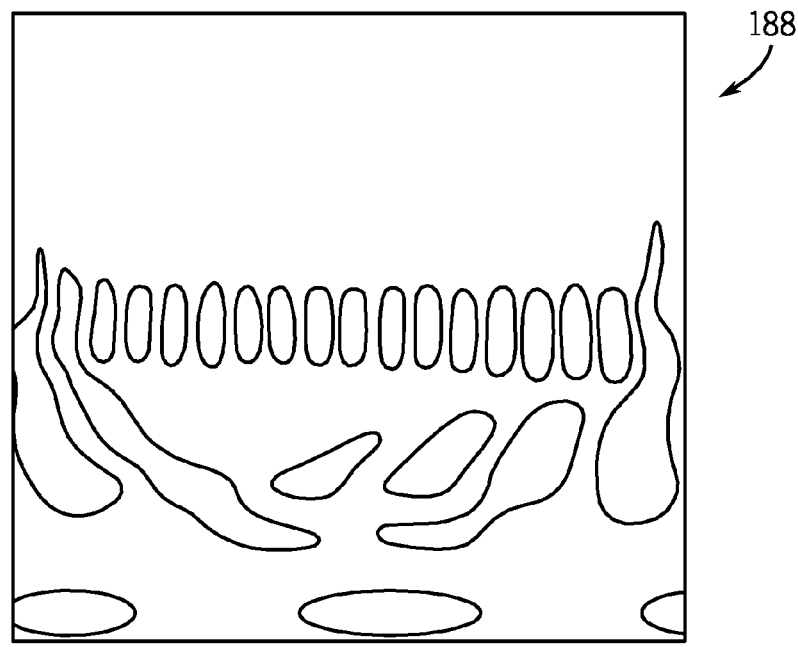
FIGS. 12-14 illustrate a method of applying a wavelet signature to photon density wave data and determining whether a pattern is present in the wavelet transformation of the photon density wave data.
Figure 13:
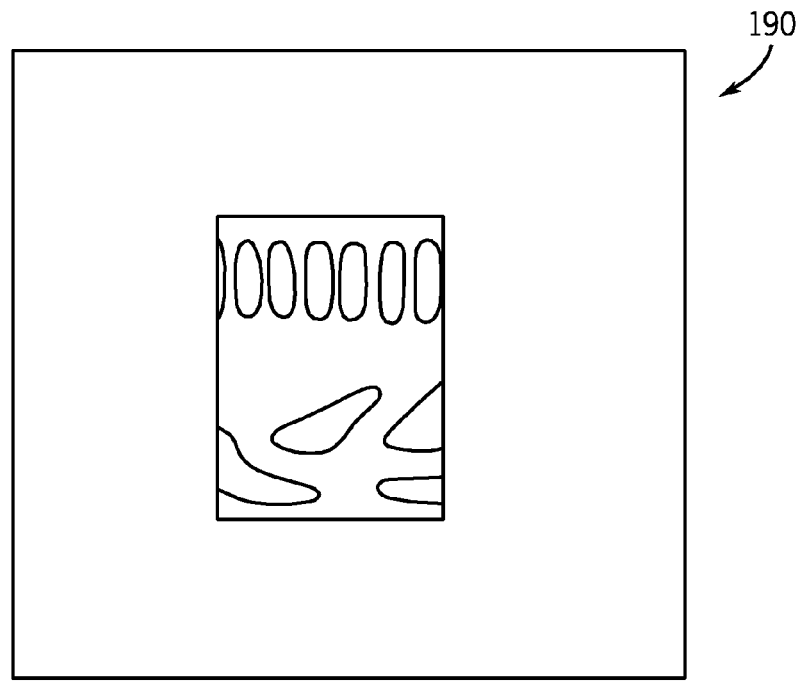
Figure 14:
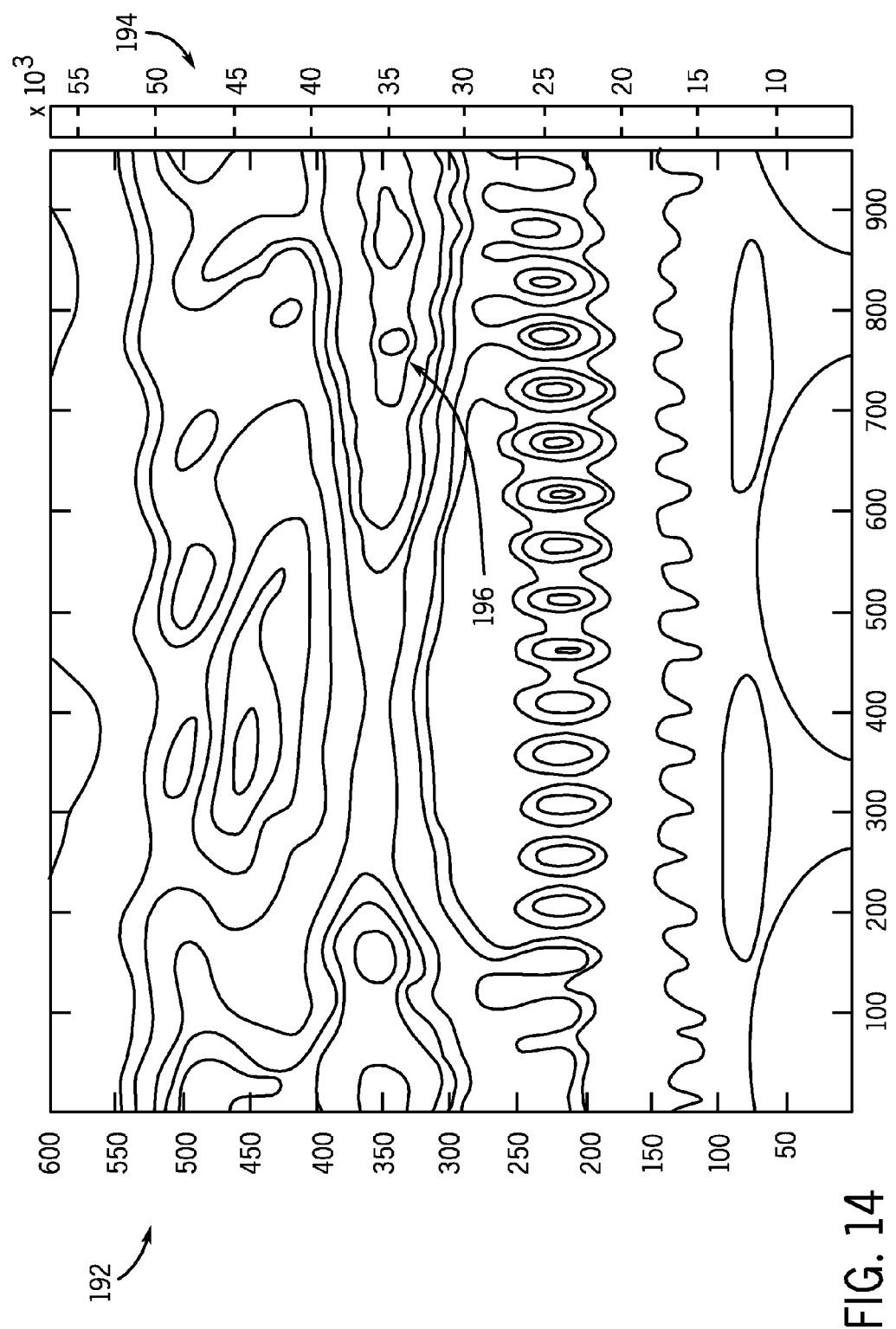

In one or more embodiments, a pattern may be identified by developing various wavelet signatures with which to compare a PDW signal. FIGS. 12-14 depict one example of how a scalogram 188 (FIG. 12) of a PDW signal may be analyzed in view of a wavelet signature 190 (FIG. 13) to determine the presence of some pattern of interest exemplified by the wavelet signature 190. In some embodiments, a set of wavelet signatures may be developed to enable the identification of various physiological conditions.

In one embodiment, the scalogram 188 may be cross-correlated with the wavelet signature 190 to determine whether the pattern of interest is present in the scalogram 188. Various techniques, such as the cross correlation and threshold techniques discussed with respect to FIGS. 9-11, may be used to determine whether the pattern, as typified by wavelet signature 190, is present in the scalogram 188. Thus, in one embodiment, one or more wavelet signatures 190 may be processed (e.g., cross-correlated) with the scalogram 188 to produce a combined image, as in the image 192 of FIG. 14. The image 192 may be analyzed (e.g., using various image processing techniques and/or facial recognition technologies) to determine whether the patterns are present. In one embodiment, the intensity throughout the image 192 may be analyzed (e.g., using an intensity scale 194) to detect instances where the intensity in the image 192 meets or surpasses some threshold. For example, the present techniques may identify a pattern 196 at some threshold intensity, and the presence of the pattern 196 may indicate one or more physiological conditions.

While the disclosure may be susceptible to various modifications and alternative forms, specific embodiments have been shown by way of example in the drawings and have been described in detail herein. However, it should be understood that the embodiments provided herein are not intended to be limited to the particular forms disclosed. Rather, the various embodiments may cover all modifications, equivalents, and alternatives falling within the spirit and scope of the disclosure as defined by the following appended claims.

What is claimed is:

1. A monitor, comprising:
   a display;

a connector port configured to receive a signal generated in response to propagation of photon density waves through tissue; and data processing circuitry configured to:
derive a phase signal and a plethysmography signal from the received signal, wherein changes the phase signal are indicative of changes in photon scattering and changes in the plethysmography signal are indicative of changes in absorption of photons by the tissue;

apply a continuous wavelet transform to the phase signal and to the plethysmography signal to generate a phase signal scalogram and a plethysmography signal scalogram, respectively;

compare the phase signal scalogram and the plethysmography signal scalogram;

identify temporal correlations between changes in photon scattering and changes in absorption of photons by the tissue based on the comparison of the phase signal scalogram and the plethysmography signal scalogram;

distinguish physiological and non-physiological components of the signal based on the temporal correlations between changes in photon scattering and changes in absorption of photons by the tissue, wherein physiological components are identified at temporal locations where changes in photon scattering correlate to changes in absorption of photons by the tissue, and non-physiological components are identified at temporal locations where changes in photon scattering do not correlate to changes in absorption of photons by the tissue;

generate patient physiological data based on at least the physiological components of the signal; and display the patient physiological data on the display.

2. The monitor, as set forth in claim 1, wherein the monitor is configured to estimate a total number of scattering particles.

3. The monitor, as set forth in claim 1, wherein the monitor is configured to estimate oxygen saturation based on the physiological component of the signal.

4. The monitor of claim 1, wherein the photon density waves are modulated at a frequency of between approximately 50 MHz to 3 GHz prior to propagation through the tissue.

5. A monitoring system, comprising:
a sensor configured to acquire photon density wave data when positioned on a patient; and
a monitor in communication with the sensor, wherein the monitor is configured to:
receive the photon density wave data from the sensor;
derive a phase signal and a plethysmography signal from the photon density wave data, wherein changes in the phase signal correspond to photon scattering and changes in the plethysmography signal correspond to absorption of photons by tissue of the patient;
apply a continuous wavelet transform to the phase signal and to the plethysmography signal to generate a phase signal scalogram and a plethysmography signal scalogram, respectively;
compare the phase signal scalogram to the plethysmography signal scalogram;
distinguish between physiological and non-physiological aspects of the photon density wave data based on whether the comparison indicates that changes in photon scattering temporally correlate with changes in absorption of photons by the tissue, wherein physiological aspects are identified at temporal locations where changes in photon scattering correlate to changes in absorption of photons by the tissue, and non-physiological aspects are identified at temporal locations where changes in photon scattering do not correlate to changes in absorption of photons by the tissue.

6. The monitoring system of claim 5, wherein the photon density wave data comprises information relating to a total number of particles at a tissue site where the sensor is positioned on the patient and information relating to a ratio of different types of particles at the tissue site.

7. The monitoring system of claim 5, wherein the monitor is configured to identify a physiological condition based on at least the physiological aspect of the photon density wave data.

8. The monitoring system of claim 5, comprising an emitter and a modulator configured to modulate light emitted by the emitter to generate photon density waves.

9. The monitoring system of claim 5, wherein the monitor is configured to remove the non-physiological aspects from the photon density wave data.

10. The monitoring system of claim 5, wherein the monitor is configured to estimate oxygen saturation based on the physiological aspects of the photon density wave data.

11. The monitoring system of claim 5, comprising a modulator disposed in the monitor or in the sensor, wherein the modulator is configured to modulate light emitted by an emitter of the sensor at a frequency between approximately 50 MHz to 3 GHz to generate resolvable photon density waves.

* * * * *